(12) United States Patent
Bala et al.

(10) Patent No.: US 11,134,848 B2
(45) Date of Patent: Oct. 5, 2021

(54) MOBILE HYPERSPECTRAL CAMERA SYSTEM AND HUMAN SKIN MONITORING USING A MOBILE HYPERSPECTRAL CAMERA SYSTEM

(71) Applicants: Raja Bala, Allen, TX (US); Sourabh Ravindran, Dallas, TX (US); Hamid Rahim Sheikh, Allen, TX (US); Youngjun Yoo, Plano, TX (US); Michael Oliver Polley, Garland, TX (US)

(72) Inventors: Raja Bala, Allen, TX (US); Sourabh Ravindran, Dallas, TX (US); Hamid Rahim Sheikh, Allen, TX (US); Youngjun Yoo, Plano, TX (US); Michael Oliver Polley, Garland, TX (US)

(73) Assignee: Samsung Electronics Co., Ltd., Suwon-si (KR)

( * ) Notice: Subject to any disclaimer, the term of this patent is extended or adjusted under 35 U.S.C. 154(b) by 318 days.

(21) Appl. No.: 15/397,982

(22) Filed: Jan. 4, 2017

(65) Prior Publication Data

US 2017/0303790 A1 Oct. 26, 2017

Related U.S. Application Data

(60) Provisional application No. 62/327,342, filed on Apr. 25, 2016, provisional application No. 62/327,338, filed on Apr. 25, 2016.

(51) Int. Cl.
*H04N 9/47* (2006.01)
*A61B 5/00* (2006.01)
(Continued)

(52) U.S. Cl.
CPC .......... *A61B 5/0077* (2013.01); *A61B 5/0075* (2013.01); *A61B 5/441* (2013.01);
(Continued)

(58) Field of Classification Search
CPC .... G01J 3/0267; G01J 3/2823; G01N 33/483; A61B 5/0013; A61B 2090/502;
(Continued)

(56) References Cited

U.S. PATENT DOCUMENTS 7,536,011 B2 5/2009 Takenaka
8,725,236 B2 5/2014 Kollias
(Continued)

FOREIGN PATENT DOCUMENTS

EP 2165669 9/2008
EP 2906158 10/2012
(Continued)

OTHER PUBLICATIONS

Chen et al., Automatic Facial Makeup Detection with Application in Face Recognition, IEEE, 2013.
(Continued)

*Primary Examiner* — Gims S Philippe
(74) *Attorney, Agent, or Firm* — John J. King

(57) ABSTRACT

A mobile hyperspectral camera system is described. The mobile hyperspectral camera system comprises a mobile host device comprising a processor and a display: a plurality of cameras, coupled to the processor, configured to capture images in distinct spectral bands; and a hyperspectral flash array, coupled to the processor, configured to provide illumination to the distinct spectral bands. A method of implementing a mobile hyperspectral camera system is also described.

36 Claims, 14 Drawing Sheets

(51) Int. Cl.
*G02B 27/01* (2006.01)
*H04N 7/18* (2006.01)
*H04N 5/225* (2006.01)
*G06K 9/22* (2006.01)
*G06K 9/20* (2006.01)
*G06T 7/11* (2017.01)
*G06T 7/00* (2017.01)
*H04N 5/232* (2006.01)
*H04N 5/33* (2006.01)
*A61B 5/103* (2006.01)
*H04N 9/04* (2006.01)
*A61B 90/50* (2016.01)

(52) U.S. Cl.
CPC .......... *A61B 5/7445* (2013.01); *G02B 27/017* (2013.01); *G06K 9/2018* (2013.01); *G06K 9/22* (2013.01); *G06T 7/0012* (2013.01); *G06T 7/11* (2017.01); *H04N 5/2256* (2013.01); *H04N 5/2257* (2013.01); *H04N 5/2258* (2013.01); *H04N 5/23293* (2013.01); *H04N 5/332* (2013.01); *H04N 7/181* (2013.01); *H04N 7/185* (2013.01); *A61B 5/1032* (2013.01); *A61B 5/445* (2013.01); *A61B 5/486* (2013.01); *A61B 5/6898* (2013.01); *A61B 5/7264* (2013.01); *A61B 5/744* (2013.01); *A61B 5/7485* (2013.01); *A61B 2090/502* (2016.02); *A61B 2562/0233* (2013.01); *A61B 2562/04* (2013.01); *A61B 2562/046* (2013.01); *G02B 2027/014* (2013.01); *G02B 2027/0138* (2013.01); *G02B 2027/0156* (2013.01); *G02B 2027/0178* (2013.01); *G06T 2207/10024* (2013.01); *G06T 2207/30088* (2013.01); *G06T 2207/30201* (2013.01); *H04N 9/04557* (2018.08)

(58) Field of Classification Search
CPC ........ A61B 2562/0233; A61B 2562/04; A61B 2562/046; A61B 5/0075; A61B 5/0077; A61B 5/1032; A61B 5/441; A61B 5/445
USPC .................................. 348/77, 234; 382/128
See application file for complete search history.

(56) References Cited

U.S. PATENT DOCUMENTS

| | | | |
|---|---|---|---|
| 8,855,412 B2 | 10/2014 | Quan | |
| 8,879,869 B2 | 11/2014 | Zamfir et al. | |
| 8,908,904 B2 | 12/2014 | Santos et al. | |
| 9,002,128 B2 | 4/2015 | Tanaka | |
| 9,098,748 B2 | 8/2015 | Yano | |
| 9,160,920 B2 | 10/2015 | Getman | |
| 9,245,196 B2 | 2/2016 | Marks et al. | |
| 9,256,068 B2 | 2/2016 | Sawada | |
| 9,277,189 B2 | 3/2016 | Nishiura | |
| 2005/0270528 A1 | 12/2005 | Geshwind et al. | |
| 2010/0056928 A1* | 3/2010 | Zuzak | A61B 5/0071 600/476 |
| 2011/0134275 A1 | 6/2011 | Nguyen | |
| 2014/0213909 A1 | 7/2014 | Mestha | |
| 2014/0293091 A1* | 10/2014 | Rhoads | G01J 3/513 348/234 |
| 2014/0316235 A1* | 10/2014 | Davis | A61B 5/441 600/407 |
| 2014/0364745 A1 | 12/2014 | Patwardhan | |
| 2014/0368629 A1 | 12/2014 | Lucet-Levannier | |
| 2014/0378810 A1* | 12/2014 | Davis | A61B 5/1034 600/407 |
| 2015/0032092 A1 | 1/2015 | Adanny | |
| 2015/0044098 A1* | 2/2015 | Smart | A61B 5/0013 422/82.05 |
| 2015/0182757 A1 | 7/2015 | Levine et al. | |
| 2015/0308896 A1 | 10/2015 | Darty | |
| 2015/0358535 A1 | 12/2015 | Ciuc | |
| 2016/0014333 A1 | 1/2016 | Corcoran et al. | |
| 2016/0042513 A1* | 2/2016 | Yudovsky | G06F 19/321 382/128 |
| 2016/0048949 A1 | 2/2016 | Peng et al. | |
| 2017/0178220 A1* | 6/2017 | Chong | G06K 9/00268 |
| 2017/0367580 A1* | 12/2017 | DiMaio | A61B 5/0064 |

FOREIGN PATENT DOCUMENTS

| | | |
|---|---|---|
| EP | 17 78 9774 | 2/2019 |
| WO | 2014172671 | 6/2013 |
| WO | 2014057481 | 4/2014 |
| WO | 2014172671 | 10/2014 |
| WO | 2015013288 A2 | 1/2015 |
| WO | 2015013288 A3 | 1/2015 |
| WO | 2016094439 | 6/2016 |

OTHER PUBLICATIONS

EP Search Report, PCT/KR2017002555, published Feb. 28, 2019.
Varshovi, Facial Makeup Detection Using HSV Color Space and Texture Analysis, Concordia University Master's Thesis, 2012.

\* cited by examiner

MOBILE HYPERSPECTRAL CAMERA SYSTEM AND HUMAN SKIN MONITORING USING A MOBILE HYPERSPECTRAL CAMERA SYSTEM

This application claims priority to provisional applications having Application Ser. No. 62/327,342 filed on Apr. 25, 2016, and Application Ser. No. 62/327,338 filed on Apr. 25, 2016, both of which are incorporated by reference in their entirety.

FIELD OF THE INVENTION

An embodiment of the present invention relates generally to hyperspectral cameras, and in particular, to a mobile hyperspectral camera system and human skin monitoring using a mobile hyperspectral camera system.

BACKGROUND OF THE INVENTION

Most mobile devices such as smartphones and tablets feature a built-in camera that brings digital photography to the consumer in a convenient, accessible, and economical fashion. These cameras capture RGB images on a single sensor using color filter arrays and employ a standard imaging pipeline to recover full resolution, color-corrected images. Most devices support a single camera on each face: a rear camera for scene photography, and a front camera for portrait (selfie) photography.

One class of cameras employs hyperspectral (or multi-spectral) imaging to capture many (e.g., greater than 3) optical bands within and possibly outside of the visible spectrum. However, these hyperspectral camera systems are costly and cumbersome, and can be operated only by a skilled specialist.

Human skin is the largest organ, and thus skin condition is an important marker of overall health and well-being. Statistics relay that approximately 1 in 3 consumers worldwide care deeply about their skin and will invest towards products, a regimen and a lifestyle that promotes healthy skin. A crucial aspect of maintaining good skin health is continuous and preventive monitoring. Since most skin conditions can be detected visually and non-invasively, digital imaging technology is an appealing tool for skin monitoring.

The detection of cosmetics applied on skin can be desirable for several reasons. First, daily makeup removal is an important step to prevent chronic skin damage; and hence an automatic method to detect if all makeup has been removed from the face is desirable. Conversely the same method can be used to detect proper application of protective cosmetics such as sunscreen or hydrating oil. Finally, certain cosmetics can interfere with the first task of skin monitoring, and hence automatic cosmetics detection can serve as a useful check during skin monitoring. Several techniques have been proposed, all of which use standard RGB imaging and exhibit limited accuracy.

For the foregoing reasons, there is a need for a mobile hyperspectral camera having a convenient and affordable form factor that can be used in applications such as, for example, skin monitoring and the detection of cosmetics on the skin.

SUMMARY OF THE INVENTION

A mobile hyperspectral camera system is described. The mobile hyperspectral camera system comprises a mobile host device comprising a processor and a display: a plurality of cameras, coupled to the processor, configured to capture images in distinct spectral bands; and a hyperspectral flash array, coupled to the processor, configured to provide illumination to the distinct spectral bands.

Another mobile hyperspectral camera system comprises a mobile host device comprising a processor and a display: a camera, coupled to the processor, configured to capture images and video in distinct spectral bands; and a hyperspectral flash array, coupled to the processor, configured to provide illumination to distinct spectral bands, wherein the hyperspectral flash array is distributed on a surface of the mobile hyperspectral camera system.

A method of implementing a mobile hyperspectral camera system is also described. The method comprises implementing a mobile host device comprising a processor and a display: configuring a plurality of cameras, coupled to the processor, to capture images in distinct spectral bands; and configuring a hyperspectral flash array, coupled to the processor, to provide illumination to distinct spectral bands.

Another method for monitoring skin using a hyperspectral camera system comprises capturing images of skin regions in distinct spectral bands; identifying regions of interest (ROIs) from the skin regions; spatially aligning the images at distinct spectral bands; analyzing the ROIs for a particular skin trait, wherein the analyzing includes incorporating contextual factors; and presenting contextual analysis on a display of the hyperspectral camera system.

Another method of monitoring skin using a hyperspectral camera system comprises capturing image or video of skin regions in distinct spectral bands; identifying regions of interest (ROIs) from the skin regions; spatially aligning the image or video at distinct spectral bands; analyzing the ROIs for a presence of cosmetics, wherein the analyzing includes incorporating contextual factors; and presenting contextual analysis on the hyperspectral camera system.

Other features will be recognized from consideration of the Detailed Description and the Claims, which follow.

DETAILED DESCRIPTION

While the specification includes claims defining the features of one or more implementations of the invention that are regarded as novel, it is believed that the circuits and methods will be better understood from a consideration of the description in conjunction with the drawings. While various circuits and methods are disclosed, it is to be understood that the circuits and methods are merely exemplary of the inventive arrangements, which can be embodied in various forms. Therefore, specific structural and functional details disclosed within this specification are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting, but rather to provide an understandable description of the circuits and methods. For example, claim language such as "at least one of A, B, or C" means only A, only B, only C, or any combination of A, B, and C.

The systems and methods set forth below disclose a mobile hyperspectral camera system comprising a mobile host device connected to two or more cameras capturing images in distinct spectral bands, a hyperspectral flash array for illuminating the scene in distinct spectral bands during photography, and a display and user interface for presenting hyperspectral images and analysis in real time. In a preferred embodiment, the mobile device is a smartphone, and the hyperspectral cameras and flash array are embedded into the device. Several alternative variants are disclosed, including a removable accessory panel comprising hyperspectral filters, which may be implemented as a sleeve as will be described in more detail below, and/or illumination. The mobile hyperspectral camera system can be used for a variety of applications including face beautification, skin monitoring, object identification, and biometrics.

A mobile hyperspectral camera system that is built into a standard consumer device such as a smartphone or tablet can offer many beneficial applications to a consumer. For example, an image of a person's face captured under near infra-red (NIR) illumination produces smooth pleasing skin tones, and can thus be combined with RGB images to enhance selfie images. Combining NIR and RGB images can also offer improved biometrics capabilities. Facial images taken under ultra-violet (UV) light reveal useful features indicative of skin health and aging. Incorporating such technologies into a common consumer mobile device such as a smartphone enables a rich suite of applications that can combine the power of hyperspectral imaging with contextual knowledge already available on the device, such as the user's environment, lifestyle, and activities.

Figure 1:
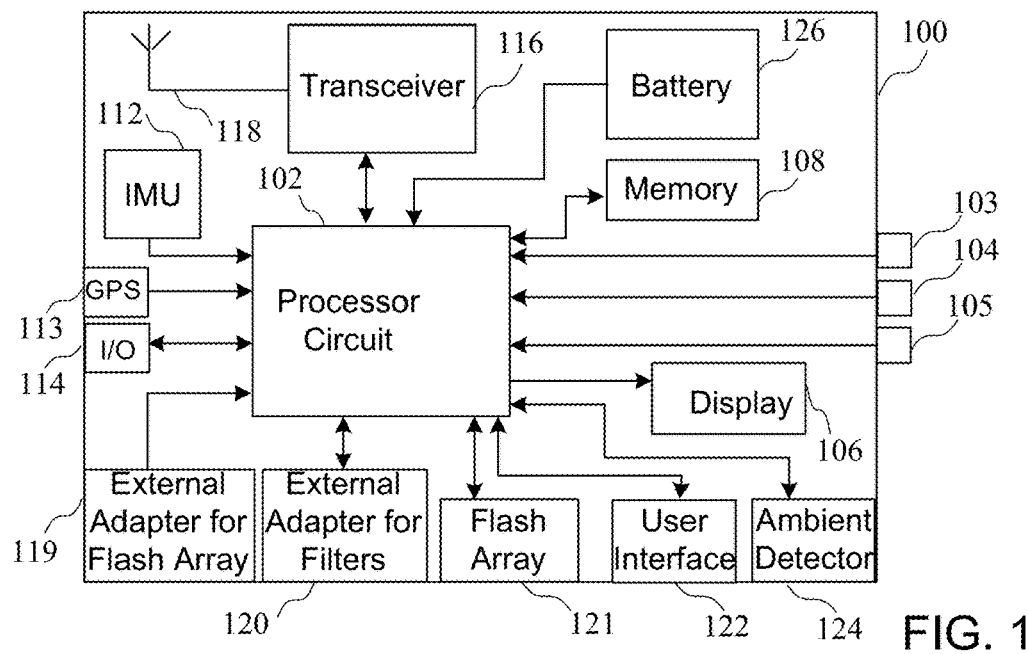
FIG. 1 is a block diagram of a device for implementing a hyperspectral camera according to an embodiment of the invention.

Turning first to FIG. 1, a block diagram of a device for implementing a hyperspectral camera is shown. In particular, a device 100 comprises a processor circuit 102 coupled to a plurality of cameras 103, 104 and 105. The device 100 could be any type of device adapted to capture a digital image using one or more camera, such as a smart phone, tablet or other electronic device. As will be described in more detail below, the plurality of cameras could include elements of a digital camera, such as a lens or other image sensing element, where the image processing could be performed by the processor circuit 102. The processor circuit could be coupled to a display 106 for displaying a captured image, and more particularly, displaying a digital image having enhanced image quality of enabling skin monitoring.

The processor circuit 102 may also be coupled to a memory 108 that enables storing information related to one or more frames of an image, or resulting digital images associated with skin or cosmetics analysis. The memory 108 could be implemented as a part of the processor circuit 102, or could be implemented in addition to any cache memory of the processor, as is well known. The processor circuit 102 may also be coupled to other elements that receive inputs or enable the capturing of a digital image. For example, an inertial measurement unit (IMU) 112 can provide various information related to the motion or orientation of the device 100, while GPS 113 provides location information associated with the device. The processor circuit 102 may receive input by way of an input/output (I/O) port 114 or a transceiver 116 coupled to an antenna 118.

The device 100 may also comprise other elements enabling the implementation of a hyperspectral camera. For example, an external adapter 119 for receiving a flash array may be included to enable the use of flash arrays having different wavelengths of light. The device 100 may also comprise an external adapter 120 for different filters. As will be described in more detail below, an external filter may be used to filter light and enable the use of a single camera for implementing a hyperspectral camera system. A flash array 121 that is part of the device 100 may also be implemented, where lighting elements of the flash array may be distributed over different locations of the device 100. A user interface 122, which may be separate from the display, or also may be a part of, or responsive to, the display, is also shown. An ambient light detector 124 may also be implemented. A battery 126 may be implemented to provide power to the processor and other elements of the device 100.

Figure 2:
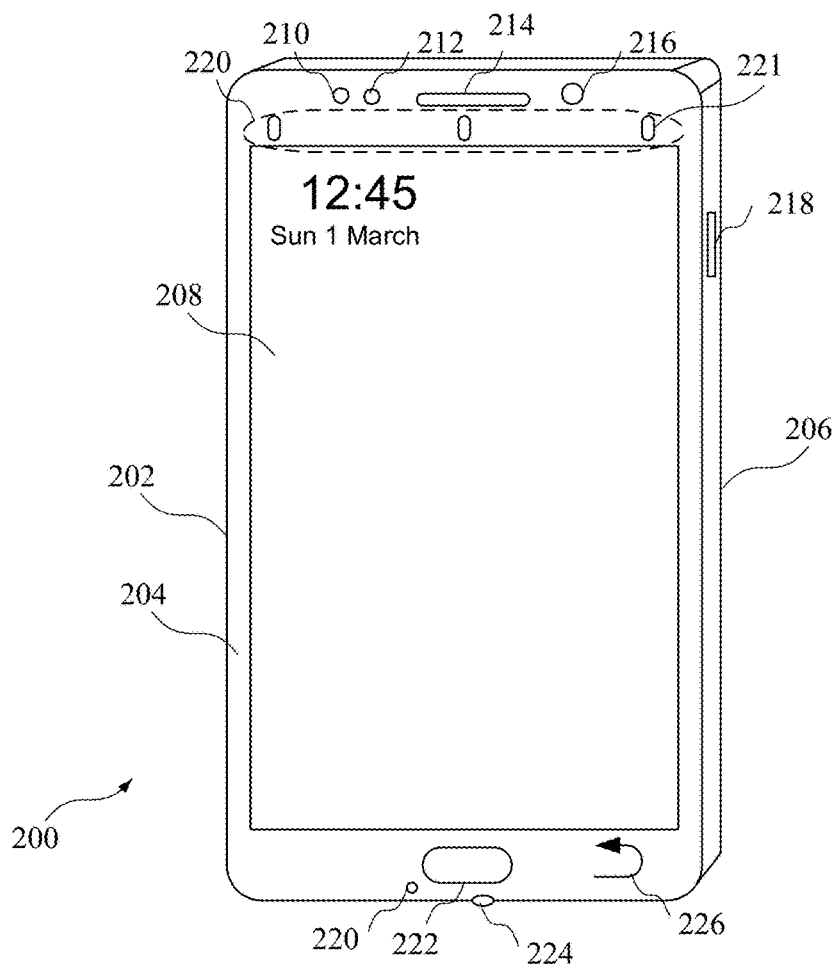
FIG. 2 is a mobile device implementing a hyperspectral camera according to an embodiment of the invention.

Turning now to FIG. 2, a mobile device 200 implementing a hyperspectral camera is shown, wherein the mobile device is a smartphone and the hyperspectral camera system is front-facing (i.e. facing the user). The mobile device 200 may implement the elements of the device 100, for example. The mobile device 200 comprises a housing 202 having front surface 204 and a back surface 206. A display 208 is provided on the front surface. One or more supplemental cameras 210 and 212 can be implemented, as will be described in more detail below. A speaker 214 can also be provided near the top of the mobile device to enable a user to hear audio while in a call or audio associated with information on the display. A main camera 216 is also provided on the front surface of the camera. The main camera 216 may be an RGB (i.e. red, blue, green) camera for example, while the supplemental cameras 210 and 212 may be implemented to detect images using other frequencies of light, such as ultra-violet (UV) or non-visible infra-red (NIR). A power button 218 enables powering the mobile device on or off. An LED flash array 220 comprising a plurality of LEDs 221 enable the capturing of images by a camera, as well as the implementation of a hyperspectral camera. A microphone 220, a home button 222, a multipurpose jack 224 and a return button 226 may be implemented at the bottom of the device. While specific elements of the mobile device 200 are shown, it should be understood that additional or different elements enabling the operation of the mobile device could be implemented.

Figure 3:
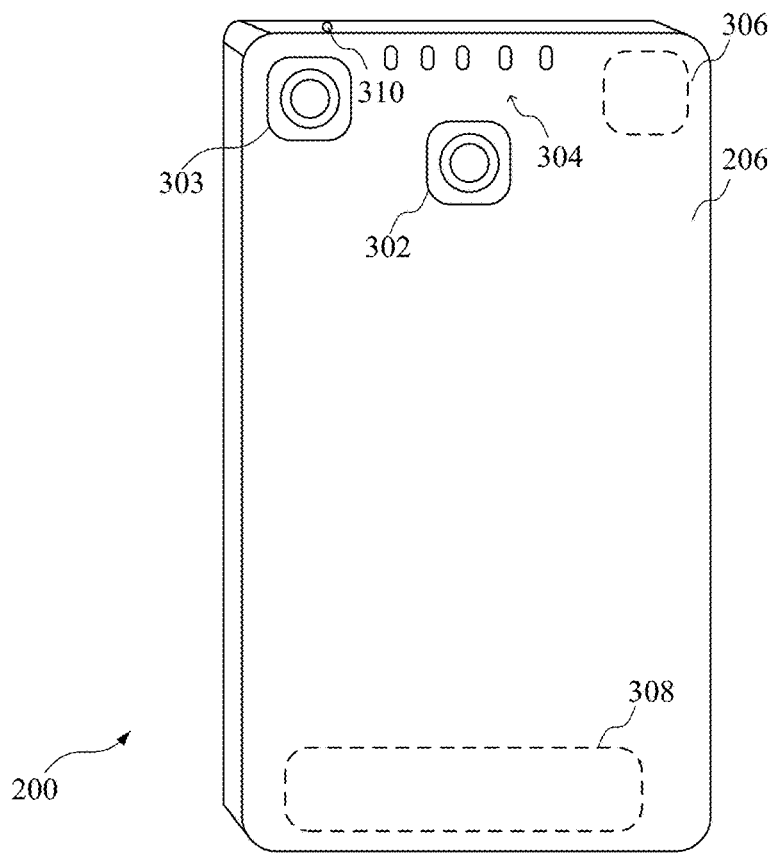
FIG. 3 is a rear side of a mobile device implementing multiple hyperspectral cameras having linear array of LEDs according to an embodiment of the invention.
Figure 4:
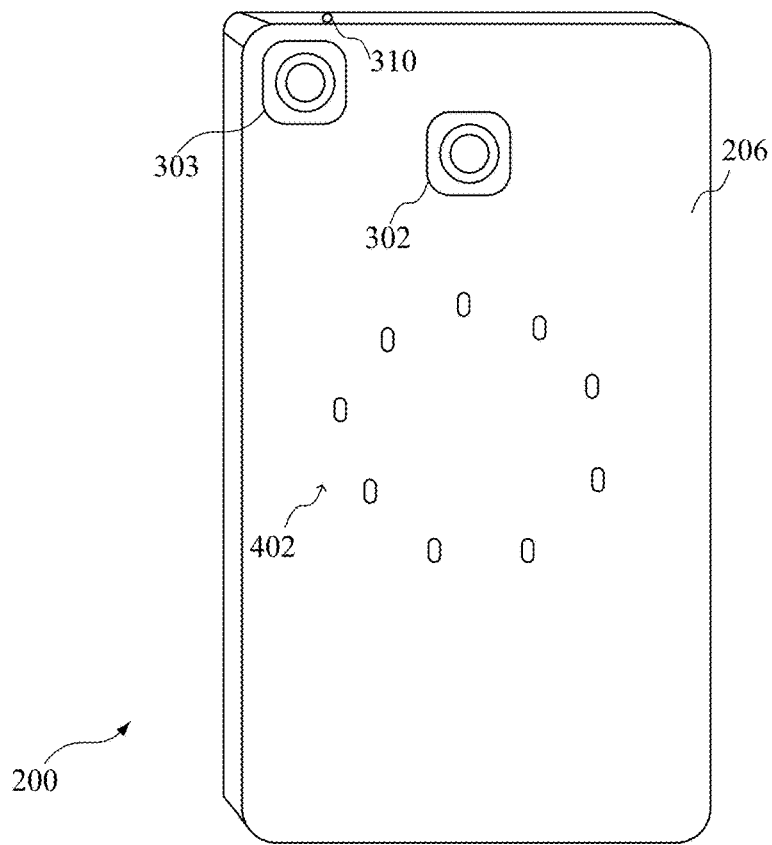
FIG. 4 is a rear side of a mobile device implementing multiple hyperspectral cameras having circular array of LEDs according to an embodiment of the invention.
Figure 5:
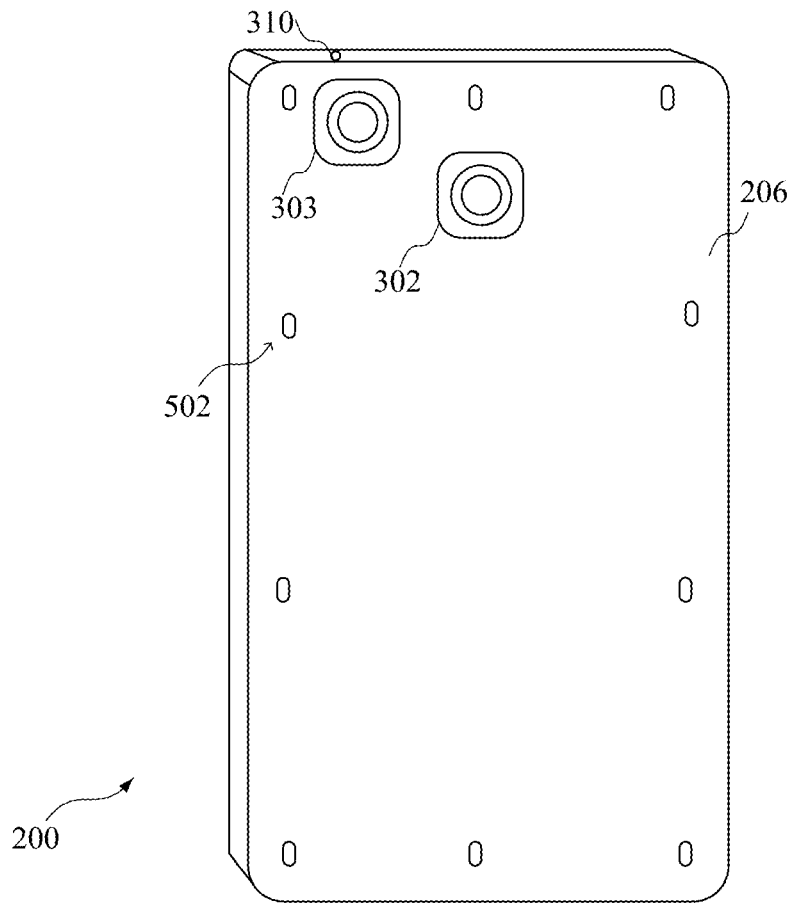
FIG. 5 is a rear side of a mobile device implementing multiple hyperspectral cameras having an array of LEDs distributed on a periphery of the device according to an embodiment of the invention.

Turning now to FIG. 3, a rear side of a mobile device implementing a hyperspectral camera having linear array of LEDs is shown. As shown in FIG. 3, the rear side 206 of the mobile device 200 of FIG. 2 comprises a first rear camera 302, a second rear camera 303, and an array of LEDs 304. The location of a GPS antenna 306 and a main antenna 308 are shown in dashed lines by way of example. A headset jack 310 may also be implemented. Various other buttons, such as volume buttons, may be implemented as necessary on the device. As shown in FIG. 4, a circular array 402 of LEDs may be implemented on the rear side of a mobile device for enabling a hyperspectral camera. Similarly, an array of LEDs may be distributed on a periphery of the device as shown in FIG. 5. It should be noted that, while LEDs are shown by way of example, any type of lighting elements could be used. Also, light of different bands could be emitted by different lighting elements to enable a hyperspectral camera.

Figure 6:
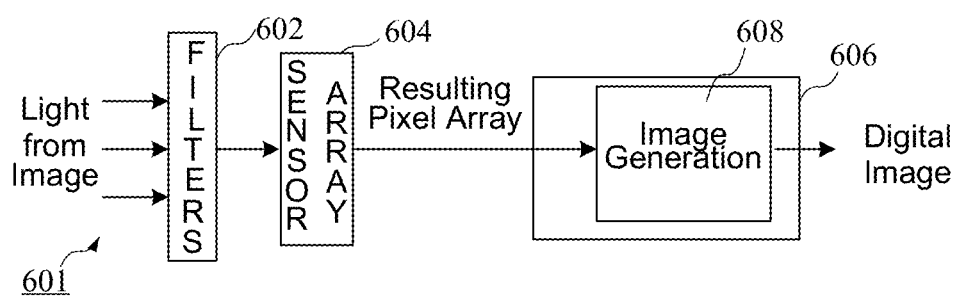
FIG. 6 is a diagram showing a digital image generated by elements of a camera according to an embodiment of the invention.

Turning now to FIG. 6, a block diagram shows a digital image being generated by elements of a camera. In particular, an image detection circuit 601 of FIG. 6 has color filters 602 coupled to receive light from a scene for which a digital image is to be generated and a sensor array 604. Common color filter arrays typically include red, green, blue color filters. It should be noted that, while various implementations described below relate to red, green, blue color filter arrays by way of example, the implementations may also apply to other color filter arrays. It should also be noted that while a three color array is described, the circuit and methods may also be applied to a four color filter array. An output of the color filter array 602 is provided to the sensor array 604. The sensor array 604 comprises a sensor in each block representing a pixel of a matrix to generate a resulting pixel array, as will be described in more detail in reference to FIG. 7. Common image sensors which may be implemented in the sensor array include a charge coupled device (CCD) or a complementary metal oxide semiconductor (CMOS) device. A processing device 606 including the image generation circuit 608 improves the quality of images generated by a device from light detected from a scene. The filters 602 and sensor array 604 may be implemented in one of the cameras 103-105, while the processing device 606 may be implemented in the processing circuit 102 for example. Further, the processing device may be implemented in a single integrated circuit device, or a plurality of integrated circuit devices of a device.

Figure 7:
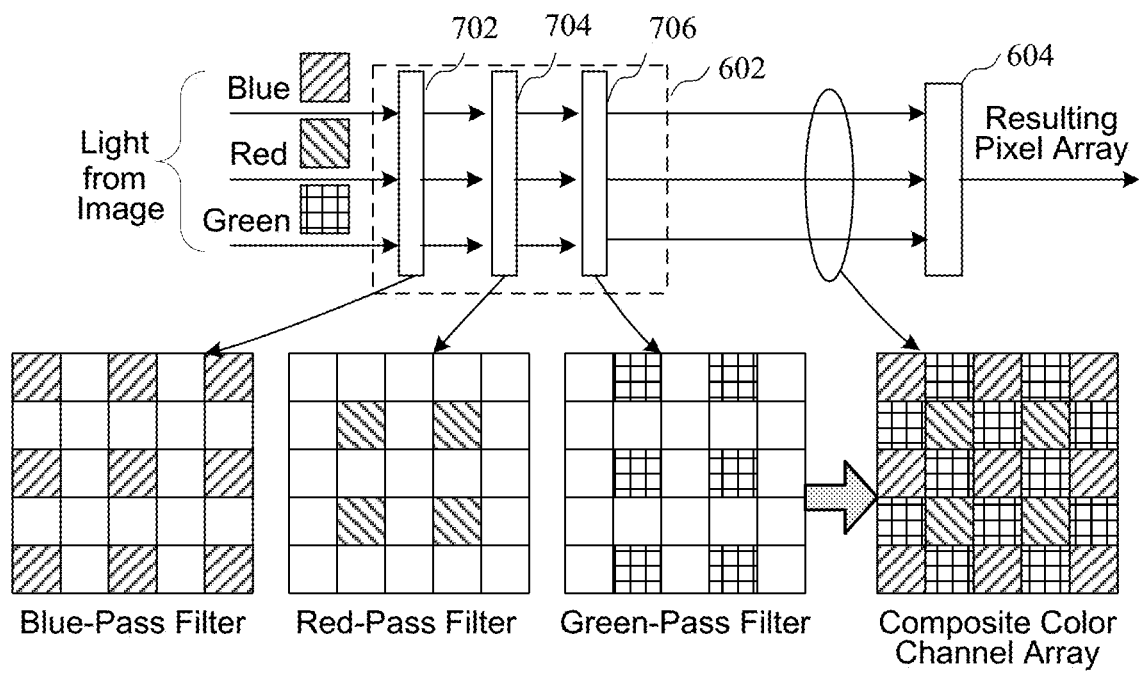
FIG. 7 is a diagram showing the generation of a pixel array according to an embodiment of the invention.

Many digital imaging devices, such as digital cameras, acquire images using an image sensor overlaid with color filters as shown in FIG. 7, such that each sensor pixel of the image sensor samples only one of the three primary colors (e.g. red, green and blue), or cyan, magenta, yellow and optionally green for example. As shown in FIG. 7, the color filters 602 may comprise a plurality of filters 702-706 for creating a composite color channel array detected by the 2-dimensional sensor array 604. According to the example of FIG. 7, a first filter 702 comprises a blue-pass filter. That is, only frequencies of light corresponding to the color blue will be passed in the boxes designated by a forward slash pattern. The other boxes (shown with no pattern) will pass all of the frequencies of light from the image which are incident at the location of the other boxes. Similarly, a second filter 704 comprises a red-pass filter which will only enable frequencies of light corresponding to the color red to pass in the boxes designated by a backward slash pattern. Finally, a third filter 706 having a green-pass filter will only enable the frequencies of light corresponding to the color green to pass in the boxes designated by a cross-hatch pattern. The light from an image is sampled and the composite of the filters 702-706 provides color channels representing intensity values to achieve the composite color channel array as is shown in FIG. 7. That is, the composite of the three filters 702-706 will allow only one color to pass in each box of the matrix. Accordingly, the resulting pixel array, also commonly referred to as a color filter array (CFA) sub-sampled image, detected by the sensor array 604 comprises a matrix associated with the image, where each pixel of the matrix is represented only by a single color component. The particular arrangement of color components as shown in FIG. 7 is commonly referred to as a Bayer CFA pattern.

Figure 8:
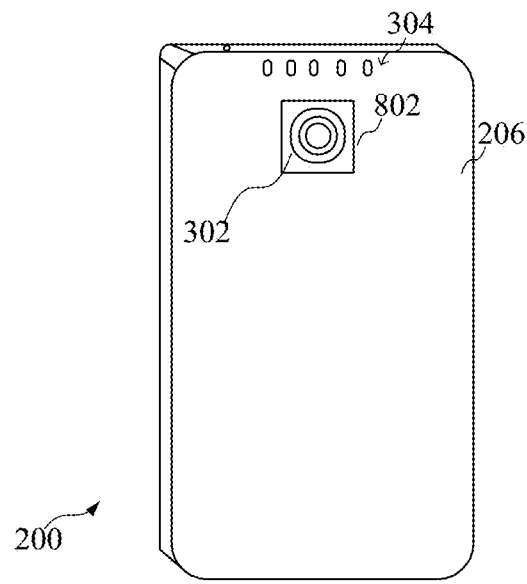
FIG. 8 is a diagram of a mobile device implementing a hyperspectral camera having a single camera according to an embodiment of the invention.

Turning now to FIG. 8, a diagram of a mobile device implementing a hyperspectral camera having a single camera is shown. More particularly, a filter 802, which may be a detachable filter for example, may be placed over a lens of the camera 302. The use of different filters enables different light to pass, and therefore enables capturing at least a fourth optical band when the filter is used. For example, the camera could be an RGB camera, but able to capture a fourth optical band when an optical filter is used. Because only a single camera is used, the different images associated with the different optical bands could be captured sequentially.

Figure 9:
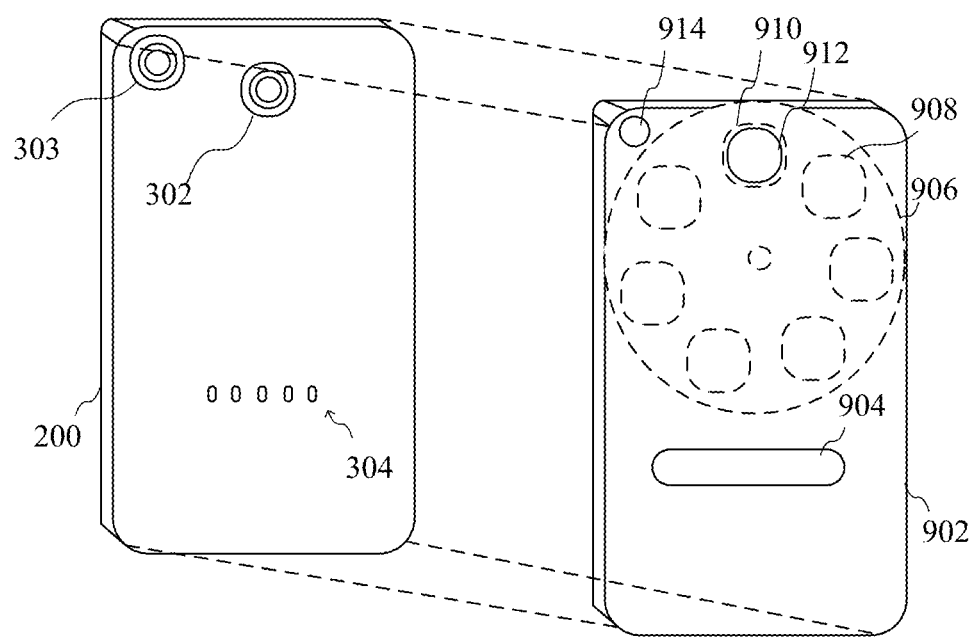
FIG. 9 is a diagram showing a sleeve used for a mobile device implementing a hyperspectral camera having multiple cameras on a rear side or the mobile device according to an embodiment of the invention.
Figure 10:
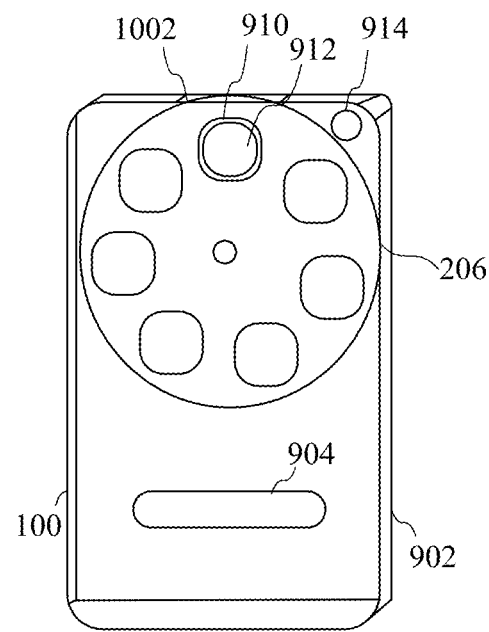
FIG. 10 shows the inside portion of the sleeve of FIG. 9 according to an embodiment of the invention.

Turning now to FIG. 9, a diagram shows a sleeve used for a mobile device implementing a hyperspectral camera system having multiple camera on a rear side, where the inside portion of the sleeve of FIG. 9 is shown in FIG. 10. As shown in FIG. 9, a sleeve 902, also commonly known as a cover or case, attachable to the device 200, containing a rotating wheel may be placed over the camera 302 and an opening 904 is provided for the flash array 304. More particularly, a rotating filter wheel 906 comprises a plurality of filters 908, each of which may be aligned with the lens of the camera. A filter 910 is aligned with an aperture 912, which may be a clear glass or plastic material, such that light may enter through the aperture and pass through the selected filter of the sleeve to the lens of the camera. By providing a movable wheel as shown, different filters may be selected without having to physically remove and replace a filter attachment for the device. A second aperture 914 is provided for the lens of the camera 303. Camera 303 may be an RGB camera, while camera 302 will be determined based upon the selected filter of the filter wheel 906. As can be seen in FIG. 10, which shows the inside of the sleeve, the wheel extends through an opening 1002 to enable the wheel to be rotated for the selection of the desired lens.

Figure 11:
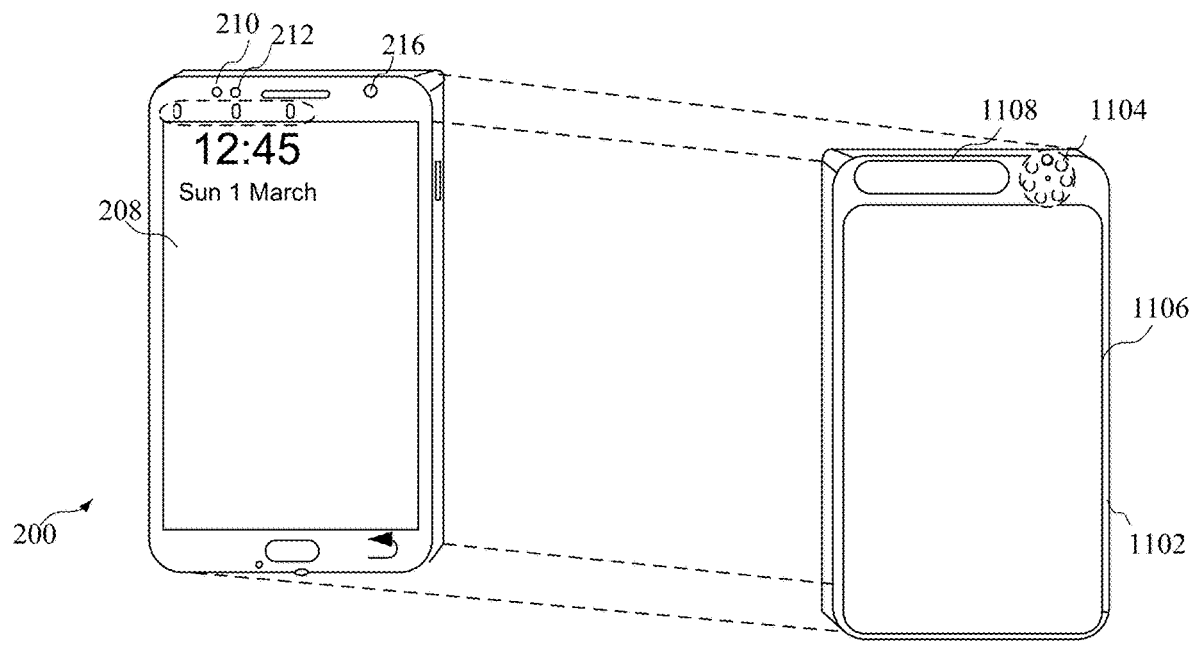
FIG. 11 is a block diagram of a diagram showing a sleeve used for a mobile device implementing a hyperspectral camera system having multiple cameras on front side of the mobile device according to an embodiment of the invention.
Figure 12:
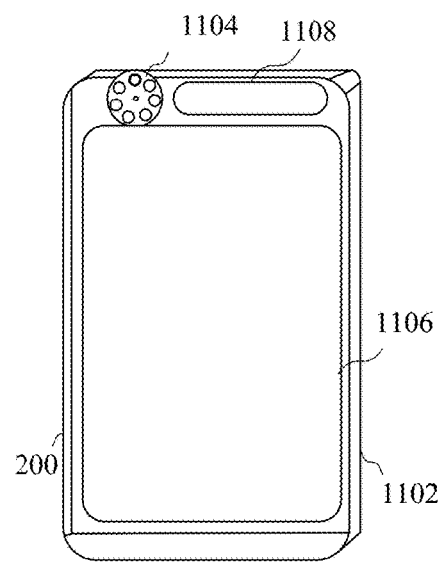
FIG. 12 shows the inside portion of the sleeve of FIG. 11 according to an embodiment of the invention.

Turning now to FIGS. 11 and 12, diagrams show a sleeve used for a mobile device implementing a hyperspectral camera system using multiple cameras on front side of the device. Unlike the sleeve 902 of FIG. 9 which fits over the back of the device, a sleeve 1102 as shown in FIG. 11 fits over the front of the device, where a filter wheel 1104 is movable to enable a selected filter to align with the lens of the camera 216, and an opening 1106 enables access to the screen 208 when the sleeve is attached to the phone. A second opening 1108 enables access to the cameras 210 and 212. As described above, cameras 210 and 212 could be an RGB camera and an NIR camera, while a filter of the filter wheel 1104 could be selected to implement a particular type of camera.

Figure 13:
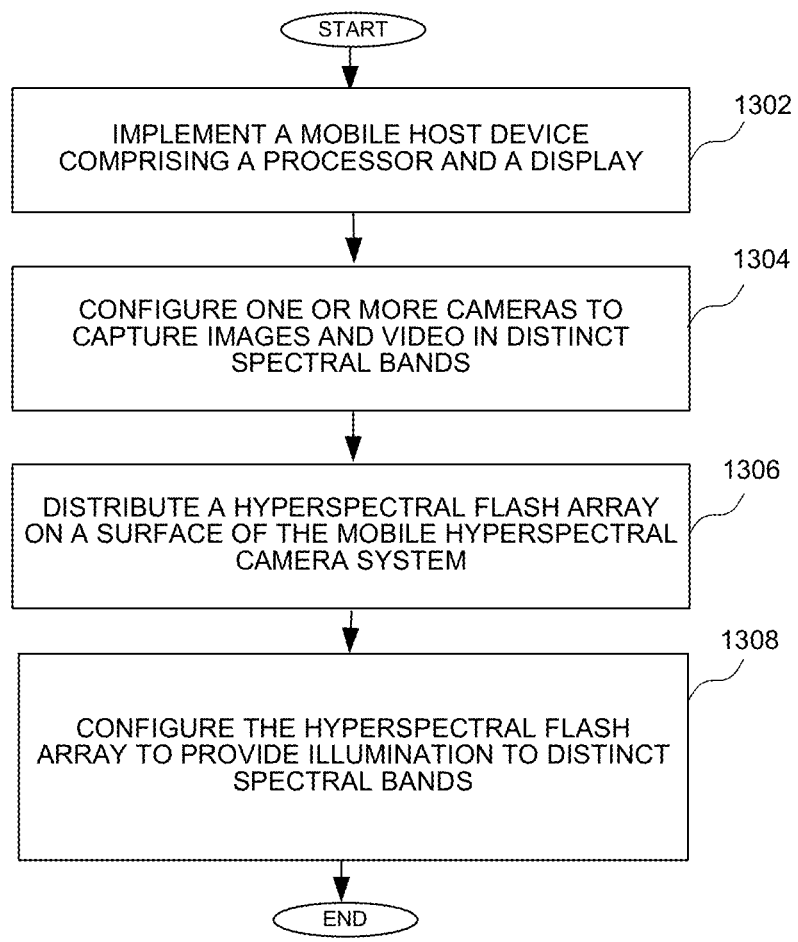
FIG. 13 is a flow chart showing a method of implementing a hyperspectral camera according to an embodiment of the invention.

Turning now to FIG. 13, a flow chart shows a method of implementing a hyperspectral camera. In particular, a mobile host device comprising a processor and a display is implemented at a block 1302. One or more cameras are configured to capture images and video in distinct spectral bands at a block 1304. A hyperspectral flash array is distributed on a surface of the mobile hyperspectral camera system at a block 1306. The hyperspectral flash array is configured to provide illumination to distinct spectral bands at a block 1308. That is, the hyperspectral flash is used with a second, non-RGB camera to acquire the desired spectral band, as described above in reference to FIGS. 9-12.

Figure 14:
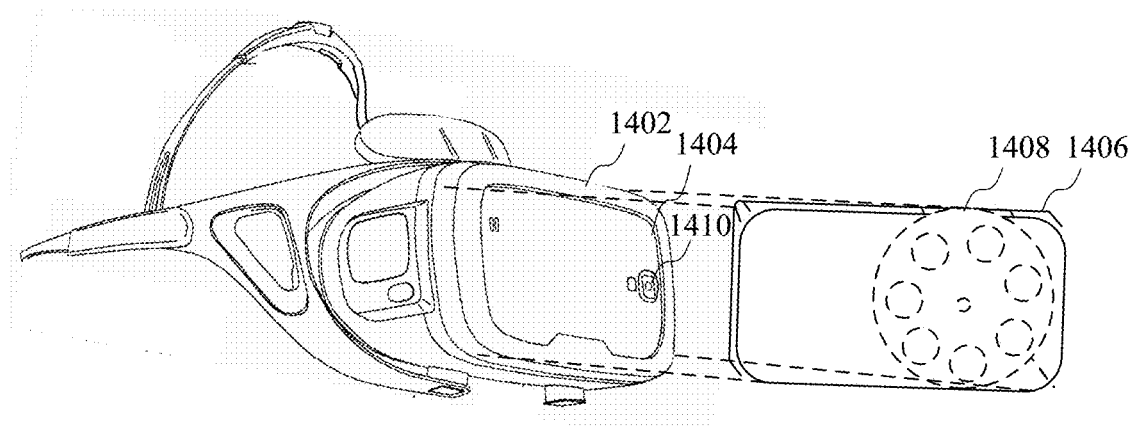
FIG. 14 is a block diagram of a head mounted device having a cover with a lens wheel for applying a lens over a camera associated with the head mounted device according to an embodiment of the invention.

Turning now to FIG. 14, a block diagram of a head mounted device (HMD) having a cover with a filter wheel for applying a filter over a camera is shown. In particular, the HMD 1402 is configured to receive a mobile device 1404, such as a smartphone. The mobile device 1404 could be implemented as described above in FIGS. 1-8, or could be some other suitable device. In one embodiment, the mobile hyperspectral camera system is inserted into an HMD such as, for example, Samsung Gear VR, or different portions of the hyperspectral camera system could be implemented in the HMD and the smartphone inserted into the HMD. The HMD can include a sleeve or cover 1406 having a filter wheel 1408 for enabling the selection of different hyperspectral filters which would align with one or more hyperspectral cameras on the camera system. In an alternative embodiment, the hyperspectral flash array is placed on the HMD rather than on the camera system.

Figure 15:
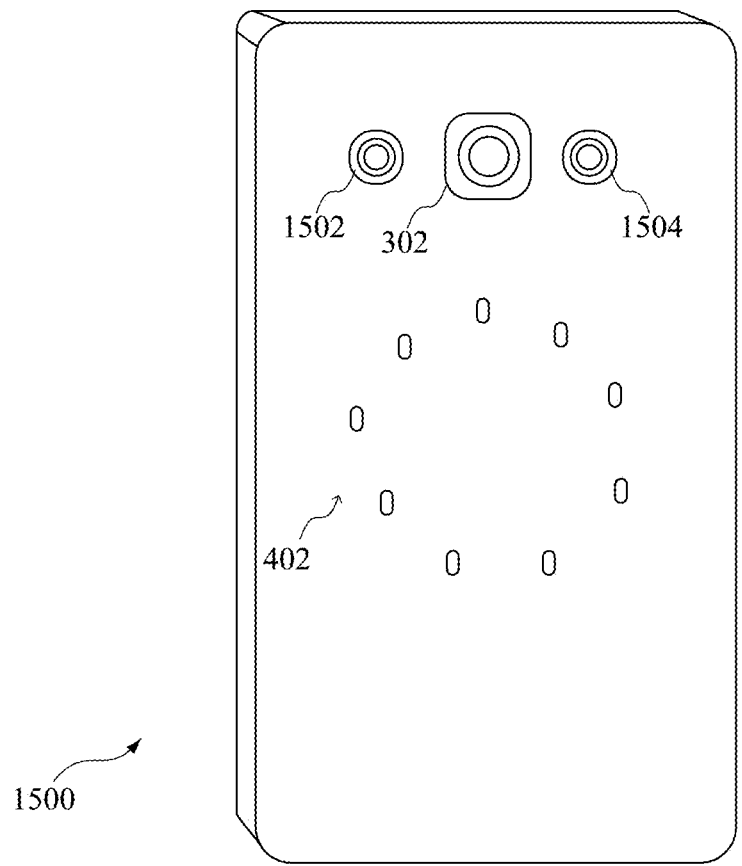
FIG. 15 is a diagram of a mobile device implementing a hyperspectral camera having a plurality of cameras according to an embodiment of the invention.

Turning now to FIG. 15, a diagram of a mobile device implementing a hyperspectral camera having a plurality of cameras is shown. According to the device 1500 of FIG. 15, a second camera 1502 is provided on one side of a main camera 302, which may be an RGB camera for example, and a third camera 1504 is provided on the other side of the camera 302. At least one of the cameras in the hyperspectral camera system is an RGB camera such as is used conventionally in consumer mobile devices. Additional cameras capture images in distinct, possibly overlapping spectral bands providing optical information beyond that from the RGB camera. In one embodiment one camera captures images in the near UV (320-400 nm) spectrum via the use of a UV filter in conjunction with a monochrome camera. In another implementation, images are captured in the near-infrared or NIR (700-1000 nm) range via the use of an NIR long-pass filter in conjunction with a monochrome camera. In addition, multiple spectral bands may be captured in a single camera via the use of a color filter array placed on top of the image sensor. For example, a color filter array with 4 filters exhibiting narrowband transmission within the visible spectrum distinct from the standard RGB filters can be employed.

The specifications of each camera, i.e. sensor size, spatial resolution, field of view, focal length, are designed based on the set of applications to be supported by the hyperspectral camera. For example, facial skin analysis will require a camera with higher sensor resolution and narrower field of view than a night vision application. Also, the cameras may be arranged in a variety of geometric configurations within the mobile host device, including linear and rectangular arrays.

In order to offer controlled and spectrally selective illumination on the object being photographed, the invention also teaches the use of a hyperspectral flash array embedded in a suitable geometric configuration within the smartphone. The array comprises one or more flash light sources for illuminating the scene in desirable wavelength bands. LED technology may be used for the light sources. In a front-facing configuration, a uniformly spaced array of light sources is placed around the edge of the smartphone, so as to offer uniform lighting with minimal shadows, as shown in FIG. 2. For a rear-facing configuration, the hyperspectral flash array may be placed in a linear or circular geometry as shown respectively in FIGS. 3 and 4. The light sources in the hyperspectral flash array are chosen to exhibit spectral properties required for a given task. Also, they can be dynamically programmed to suit the application and ambient environment. For example, in a configuration comprising white light, NIR, and UV light sources, the UV and white light sources alone may be triggered for the task of facial skin monitoring, whereas the NIR light source alone may be triggered for a night vision or biometric application. Sequential triggering of light sources in various programmable patterns is also conceivable.

The mobile host device coordinates the triggering of the hyperspectral flash array and camera capture, which may occur in parallel or sequentially. Additionally, a computational processor within the device performs necessary imaging operations, including white balance, color demosaicing, color correction, noise reduction, and image registration. While the aforementioned embodiments teach the use of a smartphone to host the hyperspectral camera, other host devices include tablets, wearable devices and robotic devices.

As described earlier, the optical filters normally embedded within the hyperspectral camera system may be housed in a detachable accessory panel. In such a scenario, different accessory panels comprising different filters can be attached to the camera system for different applications. For example, a facial skin monitoring application would warrant an accessory panel with UV filters and optical polarizers. For a night vision application, the user would attach a panel with NIR filters. In some implementations, a sleeve having a filter wheel may be used as described above. In one embodiment, the hyperspectral cameras and the hyperspectral flash array are built into the mobile host device. In another embodiment, the hyperspectral cameras and the hyperspectral flash array are physically separate from, but logically and electronically coupled to the mobile host device.

Figure 16:
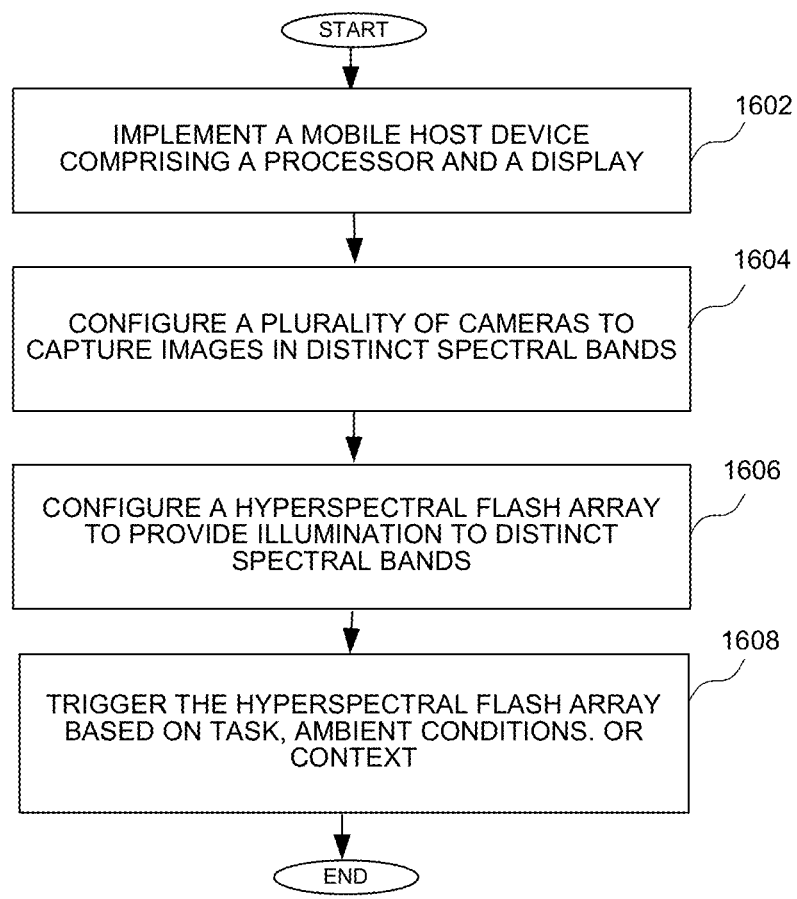
FIG. 16 is a flow chart showing a method of implementing a mobile device having a hyperspectral camera using a plurality of cameras according to an embodiment of the invention.
Figure 17:
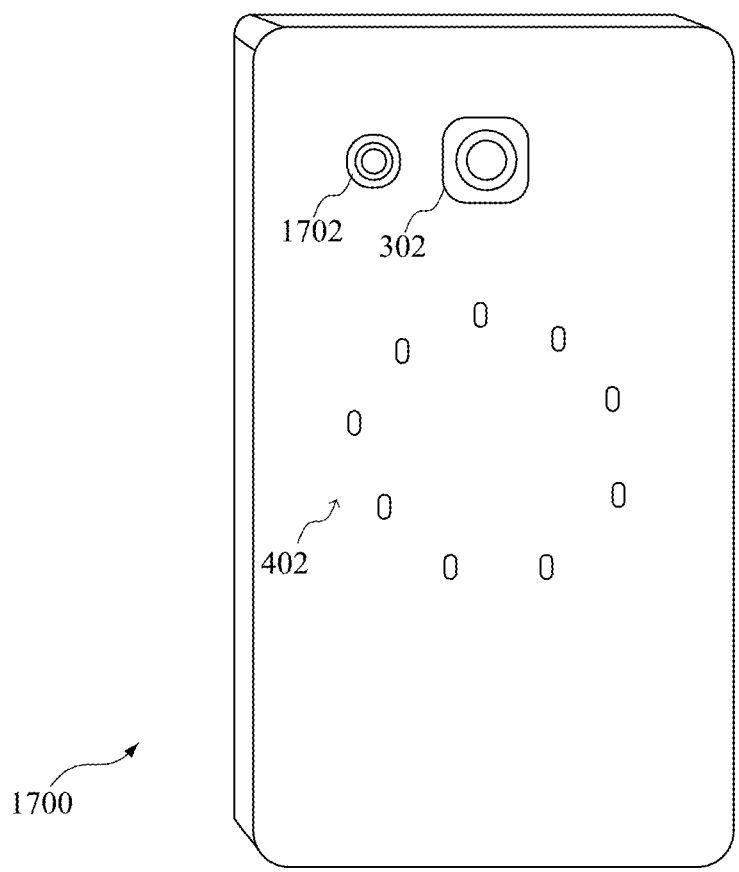
FIG. 17 is a block diagram of a device implementing a hyperspectral camera having a main RGB camera and a second camera according to an embodiment of the invention.

Turning now to FIG. 16, a flow chart shows a method of implementing a mobile device implementing a hyperspectral camera having a plurality of cameras. A mobile host device comprising a processor and a display is implemented at a block 1602. A plurality of cameras is configured to capture images in distinct spectral bands at a block 1604. A hyperspectral flash array is configured to provide illumination to distinct spectral bands at a block 1606. The hyperspectral flash array is triggered based on task, ambient conditions, or context at a block 1608. By implementing a hyperspectral flash with two or more cameras, a hyperspectral camera can easily be implemented on a mobile device, such as smart phone. As shown for example in FIG. 17, the circular array 402 of LEDs can provide a flash of different light frequencies, such as white light for the main camera 302, which may be implemented as an RGB camera, or UV light for a supplemental camera 1702, which may be a UV camera for example.

The systems and methods enable the use of a mobile hyperspectral camera to address two related applications. A first application is accurate and ongoing monitoring of skin conditions requiring attention, such as sun spots, acne, wrinkles, eczema, etc. A second application is the automatic, reliable detection of cosmetics applied to human skin. An embodiment for monitoring facial skin condition constitutes having the hyperspectral camera integrated into a consumer smartphone. The consumer takes periodic selfie images or video, for example daily or weekly, with the mobile hyperspectral camera. The images are analyzed using contextual information such as, for example, skin type, environmental temperature, humidity, and UV index. Results of the analysis are presented by way of a skin quality score, visualization maps, lifestyle, or product recommendations. The analysis is presented as ongoing feedback so that the user can track his/her skincare goals and progress.

Figure 18:
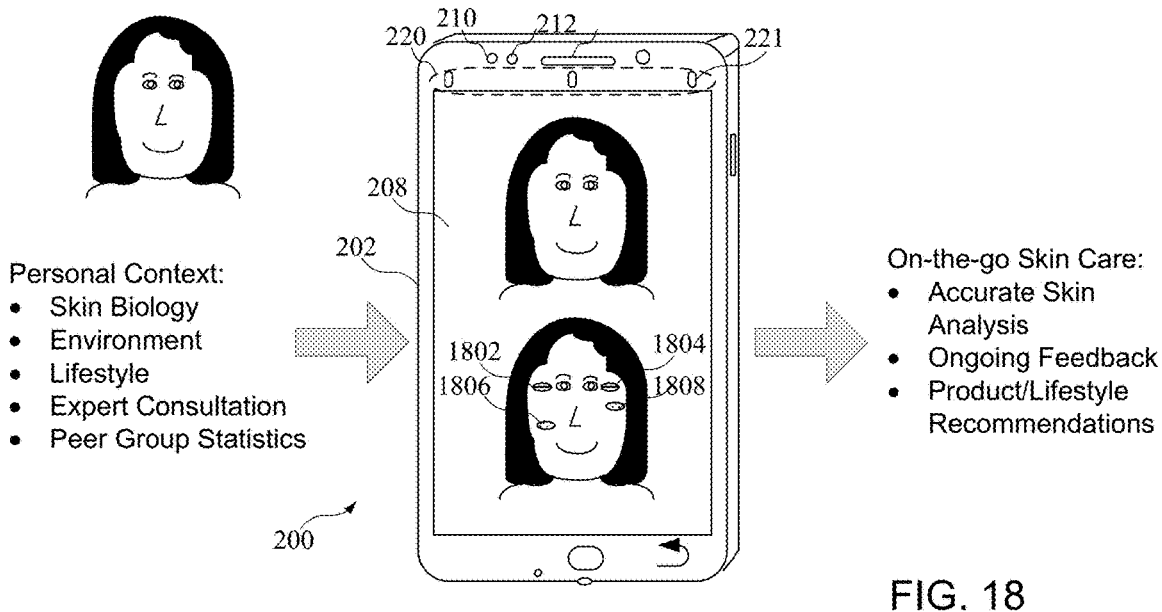
FIG. 18 shows a device for monitoring facial skin condition wherein the hyperspectral camera is integrated into a smartphone according to an embodiment of the invention.

Turning now to FIG. 18, a device for monitoring facial skin condition is shown wherein the hyperspectral camera is integrated into a smartphone. As shown in the display 208 of the mobile device, a first image may be taken with an RGB camera, while a second image may be taken with the UV camera to enable showing regions for skin analysis. As shown in FIG. 18, the second image comprises regions having defects or blemishes, such as wrinkle areas 1802 and 1804 near the eyes or other skin blemishes 1806 and 1808. The user desiring skin analysis can provide information to the mobile device to enable an output provided to the user that describes suggestions for improved skin care. By way of example, some personal context can be provided, including skin biology, environment, lifestyle, expert consultation, and peer group statistics. The output can include an accurate skin analysis, ongoing feedback, and product/lifestyle recommendations.

Figure 19:
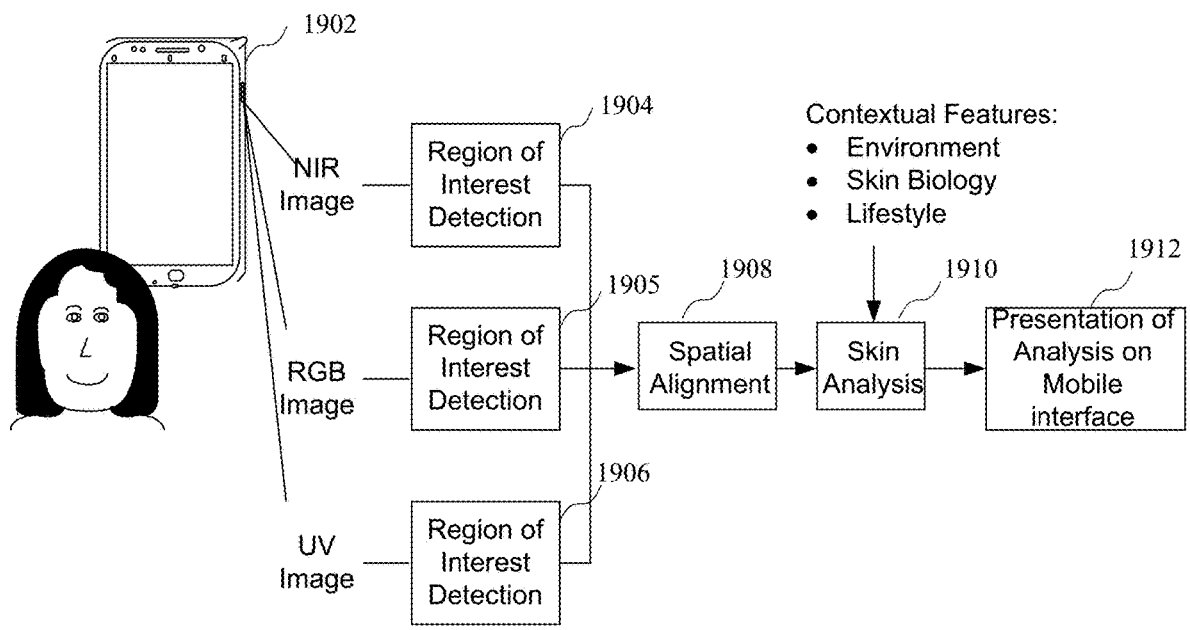
FIG. 19 shows the computation steps for performing skin monitoring according to an embodiment of the invention.
Figure 20:
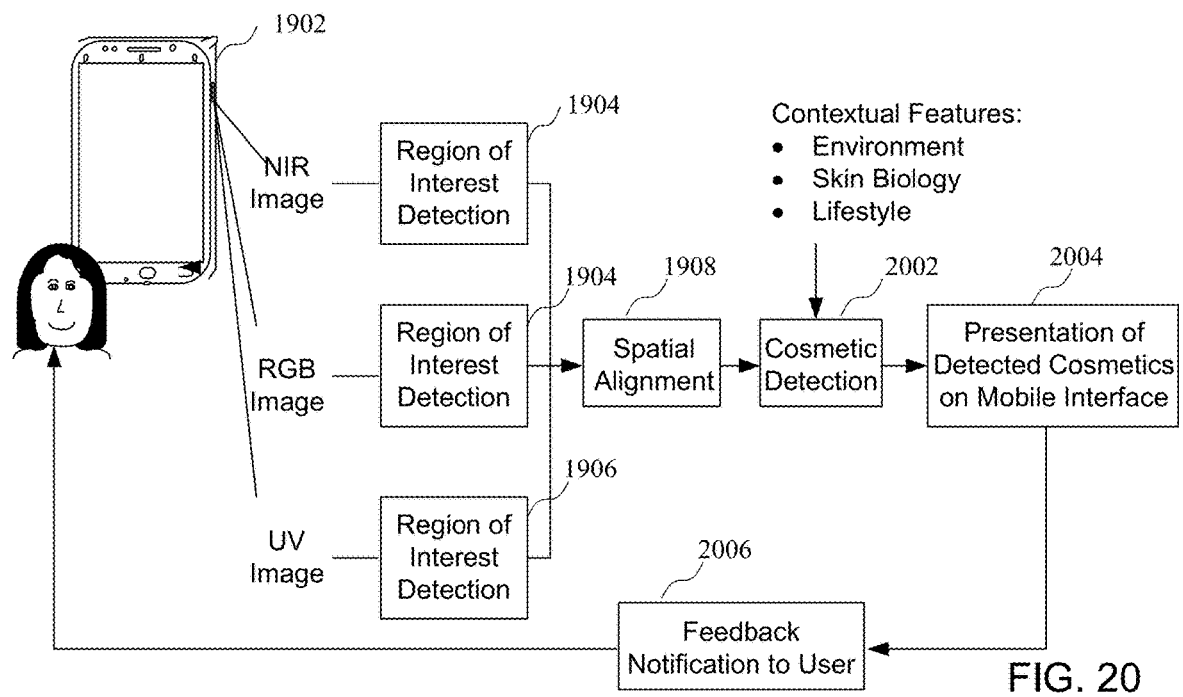
FIG. 20 shows the computation steps for performing skin monitoring including providing feedback to a user of the device according to an embodiment of the invention.

Turning now to 19, the computation steps are shown for performing skin monitoring. FIG. 19 is an algorithmic embodiment detailing the computational steps required to perform skin monitoring. In a first step, computer vision techniques such as landmark localization and color segmentation are used to detect regions of interest 1904-1906. For facial analysis, regions of interest include forehead, left cheek, right cheek, nose, and chin. Next, the images from the hyperspectral bands are spatially aligned in a spatial alignment circuit 1908. Subsequently, image analysis is performed to determine a certain skin condition or to detect presence of cosmetics. Contextual factors can be incorporated at this step to enable skin analysis by a skin analysis circuit 1910. For example, humidity can effect skin hydration and sebum content. A presentation of analysis 1912 is provided on a mobile interface. As shown in FIG. 20, a feedback notification 2002 is provided to a user of the device.

Figure 21:
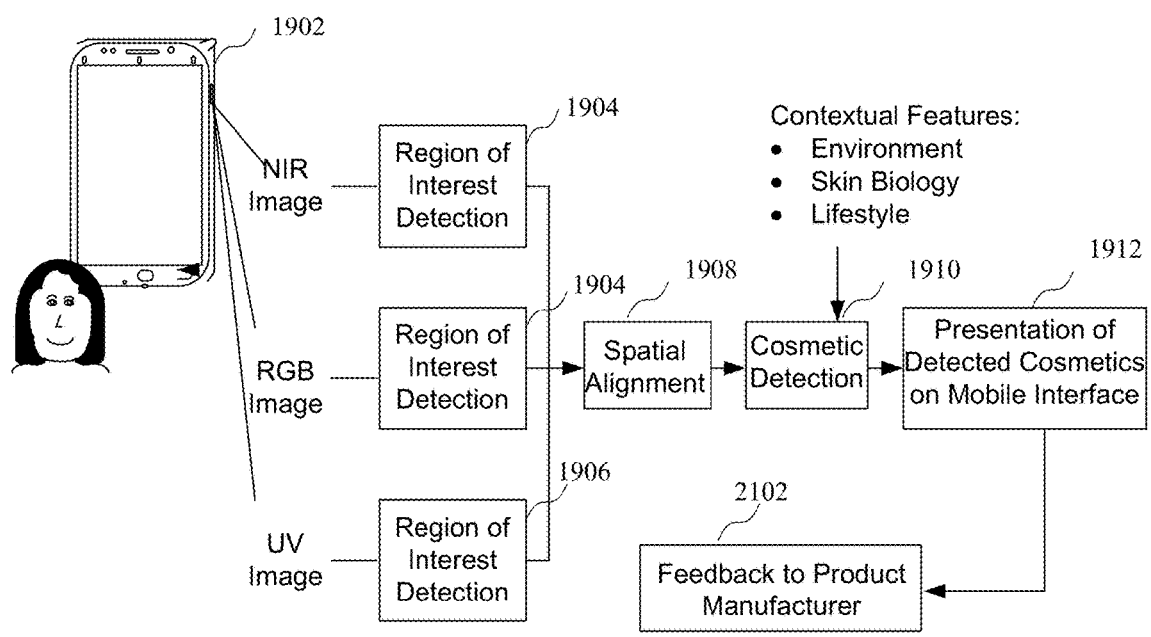
FIG. 21 shows the computation steps for performing skin monitoring including providing feedback to a product manufacturer according to an embodiment of the invention.

A second application enables detecting the presence/amount of cosmetics on human skin, including capturing image/video of human skin regions using a mobile hyperspectral camera; identifying regions of interest (ROIs) from the human skin regions; analyzing said ROIs to detect presence/amount of cosmetics application; incorporating contextual factors into skin analysis; and presenting contextual analysis in real time on mobile display/interface. Computation steps for performing skin monitoring including providing feedback to a product manufacturer of cosmetics are shown in FIG. 21. FIG. 21 provides an embodiment for detecting presence and amount of cosmetics. The steps of FIG. 21 are similar to that of FIG. 20 with a skin analysis being replaced by a cosmetics detection circuit 2102. According to the embodiment of FIG. 21, the analysis is presented offline to provide feedback to a cosmetics manufacturer to enable product quality control.

Figure 22:
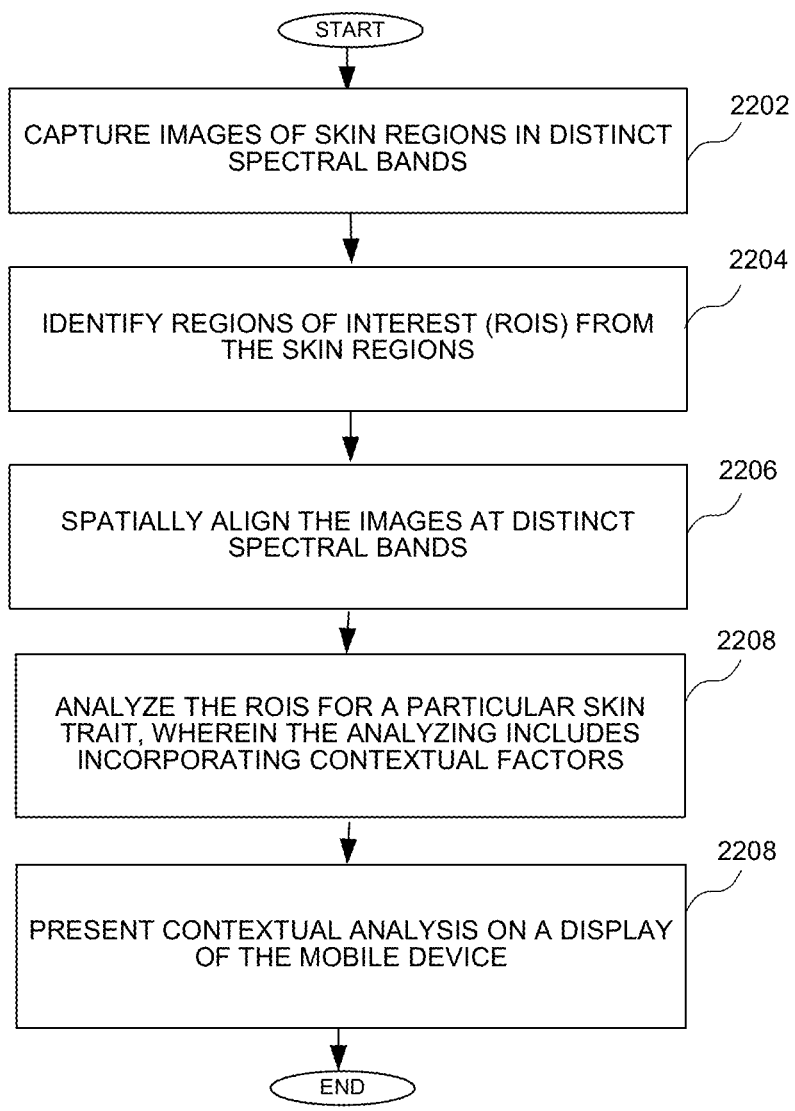
FIG. 22 is a flow chart showing a method of implementing a device having a hyperspectral camera to present contextual analysis on a display of the device according to an embodiment of the invention.

Turning now to FIG. 22, a flow chart shows a method of implementing a device having a hyperspectral camera to present contextual analysis on a display of the device. Images of skin regions in distinct spectral bands are captured at a block 2202. Regions of interest (ROIs) are identified from the skin regions at a block 2204. The images at distinct spectral bands are spatially aligned at a block 2206. The ROIs for a particular skin trait are analyzed at a block 2208, wherein the analyzing includes incorporating contextual factors. Contextual analysis is presented on a display of the mobile device at a block 2210. The method of FIG. 22 could generally relate to skin health or cosmetics, as described above.

Figure 23:
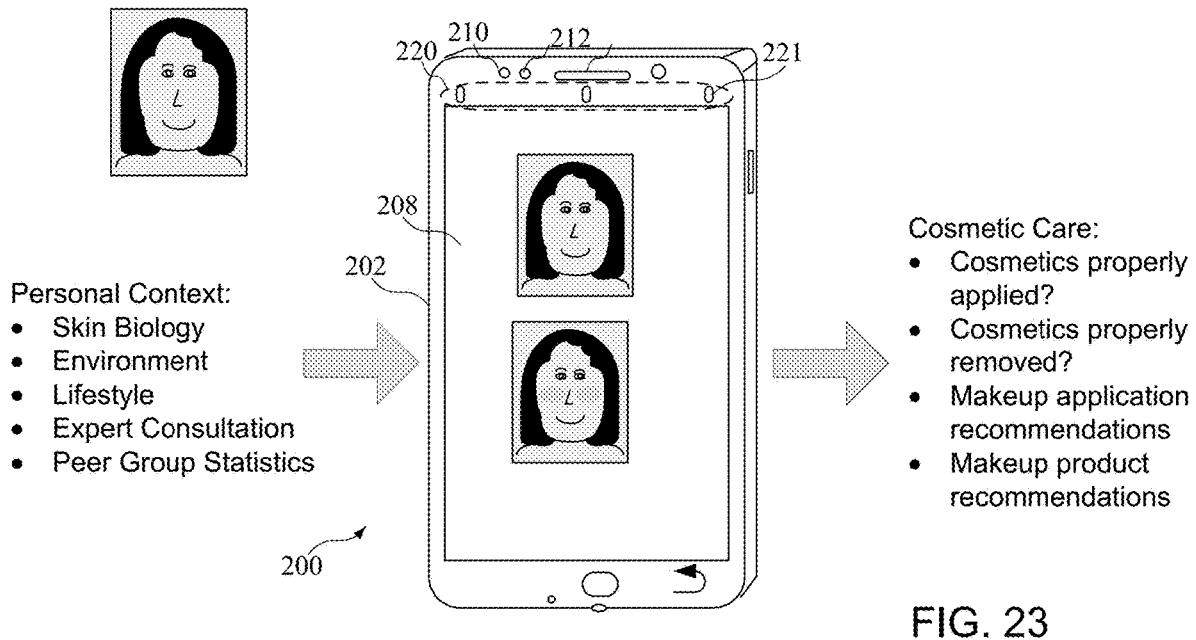
FIG. 23 is a diagram showing a mobile device enabling an analysis of the application of cosmetics according to an embodiment of the invention.

One or more embodiments of the invention disclose methods for monitoring human skin condition and detecting cosmetics on human skin using a mobile hyperspectral camera. As shown in FIG. 23, a mobile device enables an analysis of the application of cosmetics. The methods comprise the steps of hyperspectral image capture, detection of region of interest, image analysis, and data presentation. For example, the systems and methods can detect whether cosmetics have not been applied in regions where they should have been applied, or have not been removed in regions where they should have been removed. The systems and methods could also provide makeup application recommendations or makeup product recommendations.

Figure 24:
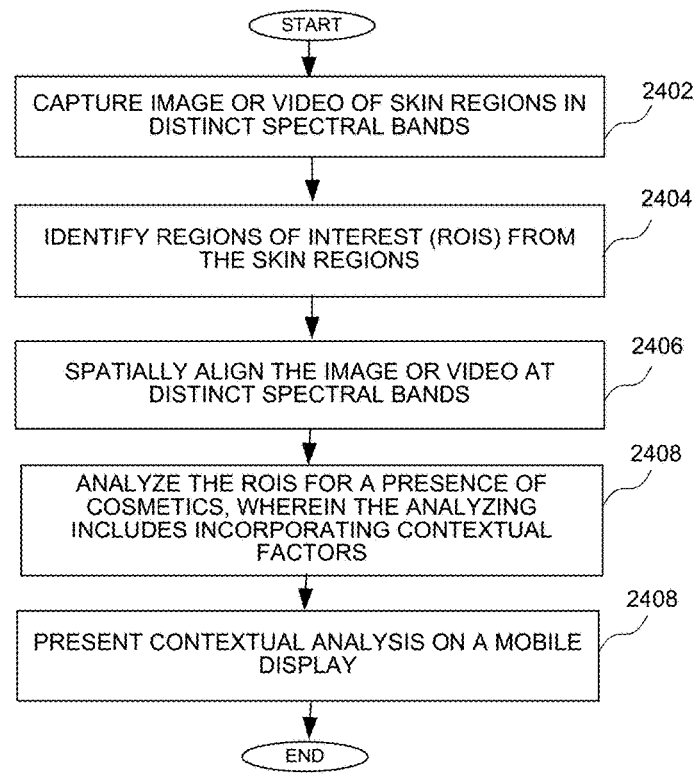
FIG. 24 is a flow chart showing a method of enabling an analysis of the application of cosmetics according to an embodiment of the invention.

Turning now to FIG. 24, a flow chart shows a method of enabling an analysis of the application of cosmetics. More particularly, an image or video of skin regions in distinct spectral bands is captured at a block 2402. Regions of interest (ROIs) from the skin regions are identified at a block 2404. The image or video at distinct spectral bands is spatially aligned at a block 2406. The ROIs are analyzed for a presence of cosmetics at a block 2408, wherein the analyzing includes incorporating contextual factors. Contextual analysis is presented on a mobile display at a block 2408.

Alternative embodiments of the invention include the following variants: a) Mobile device is one of smartphone, tablet, wearable, or robotic device; b) hyperspectral images comprise RGB, NIR, UV bands; c) analysis is performed on still images or video; d) skin regions include face, chest, back, arms, and legs; e) image analysis includes spatial image alignment across spectral bands; f) image analysis includes temporal alignment and tracking of skin features; g) ROI analysis is based on facial landmarks; h) cosmetics detected include sunscreen, foundation, oil, gloss, or lipstick; i) analysis is based on one/more of following skin texture feature descriptors: local binary patterns, Gabor filters, gray-level co-occurrence matrix, convolutional neural network features; j) color analysis is based on one/more of following color features: $1^{st}$, $2^{nd}$, $3^{rd}$ moments in RGB, HSV, and luminance; k) skin analysis is based on degree of front-surface reflection; l) image analysis employs one/more of following machine learning techniques: independent component analysis, support vector machine, regression trees, convolutional neural networks, incremental learning; m) computations and analysis are performed on mobile device vs cloud; n) contextual factors include environmental temperature, humidity, UV index, pollution, sleep habits, travel patterns, data from wearable bio-sensors that monitor pulse, or exercise.

Presentation of skin analysis on mobile device includes displaying numerical skin quality index; augmented reality visualization, highlighting skin features of interest; animation to show skin changes over time; product recommendations; lifestyle recommendations; score for percentage coverage of cosmetics application; augmented reality visualization of cosmetics application on skin; and skin analysis shared at a remote station.

It can therefore be appreciated that new devices and methods of implementing a multispectral camera have been described. It will be appreciated by those skilled in the art that numerous alternatives and equivalents will be seen to exist that incorporate the disclosed invention. As a result, the invention is not to be limited by the foregoing embodiments, but only by the following claims.

We claim:

1. A mobile hyperspectral camera system, comprising:
   a mobile host device comprising a processor and a display;
   a plurality of cameras, coupled to the processor, configured to capture images in distinct spectral bands, wherein the plurality of cameras is on a front surface having the display of the mobile host device; and
   a hyperspectral flash array, coupled to the processor, configured to provide illumination to the distinct spectral bands, wherein the hyperspectral flash array comprises a plurality of lighting elements distributed on the front surface of the mobile host device;
   wherein the hyperspectral flash array is dynamically programmable based upon an application and an ambient environment, and predetermined light sources associated with predetermined frequency bands of the hyperspectral flash array are triggered for monitoring of facial skin conditions;
   wherein the captured images are analyzed using personal contextual information associated with a user of the mobile hyperspectral camera system and personal contextual information associated with an environment of the user, and provided by at least one of (i) the mobile host device or (ii) an external device; and
   wherein feedback is provided for detected facial skin conditions.

2. The mobile hyperspectral camera system of claim 1 wherein the mobile host device is a smartphone, tablet, wearable, or robotic device.

3. The mobile hyperspectral camera system of claim 1 wherein at least one of the plurality of cameras or the hyperspectral flash array is built into the mobile host device.

4. The mobile hyperspectral camera system of claim 1 wherein at least one of the plurality of cameras or the hyperspectral flash array is external to the mobile host device.

5. The mobile hyperspectral camera system of claim 1 further comprising one or more cameras on a rear-face of the mobile host device.

6. The mobile hyperspectral camera system of claim 1 wherein the hyperspectral flash array comprises white light, NIR, or UV light sources.

7. The mobile hyperspectral camera system of claim 1 wherein the hyperspectral flash array has a linear, circular, or peripheral geometry.

8. The mobile hyperspectral camera system of claim 1 wherein the hyperspectral flash array is triggered based on a task, ambient conditions, or context.

9. The mobile hyperspectral camera system of claim 1 wherein the plurality of cameras captures images or video.

10. The mobile hyperspectral camera system of claim 1 wherein the plurality of cameras comprises at least two of: RGB, UV, NIR, or Monochromatic cameras.

11. The mobile hyperspectral camera system of claim 1 further comprising: a color filter array, wherein the color filter array is on a particular one of the plurality of cameras.

12. The mobile hyperspectral camera system of claim 1 further comprising a removable sleeve, wherein the removable sleeve comprises at least one of: a plurality of hyperspectral filters or a plurality of optical polarizers, and wherein the at least one of the plurality of hyperspectral filters and the plurality of optical polarizers is associated with a particular one of the plurality of cameras.

13. The mobile hyperspectral camera system of claim 1 wherein the mobile host device is a wearable device.

14. The mobile hyperspectral camera system of claim 13 wherein the mobile host device is a head mounted display.

15. The mobile hyperspectral camera system of claim 1 wherein the mobile host device captures images or video of skin regions in distinct spectral bands, and identifies regions of interest (ROIs) from the skin regions.

16. A mobile hyperspectral camera system, comprising:
    a mobile host device comprising a processor and a display, wherein the display is located on a front surface of the mobile host device;
    a camera, coupled to the processor, configured to capture images and video in distinct spectral bands, wherein the camera is located on the front surface of the mobile host device; and
    a hyperspectral flash array, coupled to the processor, configured to provide illumination to the distinct spectral bands, wherein lighting elements of the hyperspectral flash array are distributed on the front surface of the mobile host device;
    wherein the hyperspectral flash array is dynamically programmable based upon an application and an ambient environment, and predetermined light sources associated with predetermined frequency bands of the hyperspectral flash array are triggered for monitoring of facial skin conditions;

wherein the captured images are analyzed using personal contextual information associated with a user of the mobile hyperspectral camera system and personal contextual information associated with an environment of the user, and provided by at least one of (i) the mobile host device or (ii) an external device; and wherein feedback is provided for detected facial skin conditions.

17. The mobile hyperspectral camera system of claim 16 wherein the hyperspectral flash array has a linear, circular, or peripheral geometry.

18. The mobile hyperspectral camera system of claim 16 wherein at least one of the camera or the hyperspectral flash array is built into the mobile host device.

19. The mobile hyperspectral camera system of claim 16 wherein the hyperspectral flash array comprises white light, NIR, or UV light sources.

20. The mobile hyperspectral camera system of claim 16 further comprising a filter attachable to the outside of the mobile hyperspectral camera system.

21. The mobile hyperspectral camera system of claim 20 wherein the filter comprises a moveable element on a sleeve configured to be attached to a phone.

22. The mobile hyperspectral camera system of claim 20 wherein the filter comprises a moveable element on a cover configured to be attached to a head mounted device holding a phone.

23. A method of implementing a mobile hyperspectral camera system, the method comprising:

implementing a mobile host device comprising a processor; a display located on a front surface; and lighting elements of a hyperspectral flash array distributed on the front surface:

coupling a plurality of cameras on the front surface to the processor, wherein the plurality of cameras are configured to capture images and videos in distinct spectral bands;

coupling the hyperspectral flash array to the processor, wherein the hyperspectral flash array is configured to provide illumination to the distinct spectral bands; and analyzing the captured images using personal contextual information associated with a user of the mobile hyperspectral camera system and personal contextual information associated with an environment of the user, and provided by at least one of (i) the mobile host device or (ii) an external device;

wherein the hyperspectral flash array is dynamically programmable based upon an application and an ambient environment, and predetermined light sources associated with predetermined frequency bands of the hyperspectral flash array are triggered for monitoring of facial skin conditions; and wherein feedback is provided for detected facial skin conditions.

24. The method of claim 23 wherein the hyperspectral flash array comprises white light, NIR, or UV light sources.

25. The method of claim 23 wherein the hyperspectral flash array has a linear, circular, or peripheral geometry.

26. The method of claim 23 further comprising triggering the hyperspectral flash array based on a task, ambient conditions, or context.

27. The method of claim 23 wherein the plurality of cameras comprises at least two of: RGB, UV, NIR, or Monochromatic cameras.

28. A method of monitoring skin using a mobile hyperspectral camera system, comprising:

implementing a mobile host device comprising a processor; a display located on a front surface; a camera, coupled to the processor, located on the front surface and configured to capture images and video in distinct spectral bands; and a hyperspectral flash array, coupled to the processor, configured to provide illumination to distinct spectral bands, wherein lighting elements of the hyperspectral flash array are distributed on the front surface and predetermined light sources associated with predetermined frequency bands of the hyperspectral flash array are triggered for monitoring of facial skin conditions and the hyperspectral flash array is dynamically programmable based upon an application and an ambient environment;

capturing images of skin regions in the distinct spectral bands;

analyzing the captured images using personal contextual information associated with a user of the mobile hyperspectral camera system and personal contextual information associated with an environment of the user, and provided by at least one of (i) the mobile host device or (ii) an external device;

identifying regions of interest (ROIs) from the skin regions;

spatially aligning the captured images at the distinct spectral bands;

analyzing the ROIs for a particular skin trait, wherein the analyzing includes incorporating contextual factors; and presenting contextual analysis on a display of the hyperspectral camera system;

wherein feedback is provided for detected facial skin conditions.

29. The method of claim 28 wherein analyzing the ROIs for a particular skin trait comprises analyzing the ROIs for a particular skin condition or presence of cosmetics.

30. The method of claim 28 wherein the contextual factors comprise at least one of skin biology, environment, lifestyle, expert consultation, or peer group statistics.

31. The method of claim 28 further comprising presenting the contextual analysis to a cosmetic manufacturer for product quality control.

32. A method of monitoring skin using a mobile hyperspectral camera system, comprising:

implementing a mobile host device comprising a processor; a display located on a front surface; a camera, coupled to the processor, located on the front surface and configured to capture images and video in distinct spectral bands; and a hyperspectral flash array, coupled to the processor, configured to provide illumination to distinct spectral bands, wherein lighting elements of the hyperspectral flash array are distributed on the front surface and predetermined light sources associated with predetermined frequency bands of the hyperspectral flash array are triggered for monitoring of facial skin conditions and the hyperspectral flash array is dynamically programmable based upon an application and an ambient environment;

capturing images or video of skin regions in the distinct spectral bands;

analyzing the captured images using personal contextual information associated with a user of the mobile hyperspectral camera system and personal contextual information associated with an environment of the user and provided by at least one of (i) the mobile host device or (ii) an external device;

identifying regions of interest (ROIs) from the skin regions;

spatially aligning the images or video at the distinct spectral bands;

analyzing the ROIs for a presence of cosmetics, wherein the analyzing includes incorporating contextual factors; and presenting contextual analysis on the hyperspectral camera system;

wherein feedback is provided for detected facial skin conditions.

33. The method of claim 32 further comprising presenting the contextual analysis to a cosmetic manufacturer for product quality control.

34. The method of claim 32 wherein analyzing the ROIs for a presence of cosmetics comprises determining where cosmetics have not been applied.

35. The method of claim 32 wherein analyzing the ROIs for a presence of cosmetics comprises determining where cosmetics have not been removed.

36. The method of claim 32 further comprising providing cosmetic product recommendations.

* * * * *